United States Patent [19]
Boas et al.

[11] Patent Number: 6,076,010
[45] Date of Patent: *Jun. 13, 2000

[54] IMAGING SPATIALLY VARYING DYNAMIC MEDIA WITH DIFFUSING CORRELATION WAVES

[75] Inventors: David A. Boas; Arjun G. Yodh, both of Philadelphia, Pa.

[73] Assignee: Trustees of the University of Pennsylvania, Philadelphia, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/666,975

[22] Filed: Jun. 20, 1996

[51] Int. Cl.$^7$ ............................................. A61B 6/00
[52] U.S. Cl. ........................... 600/477; 356/337; 356/338
[58] Field of Search ..................... 128/664, 665, 128/653.1, 633; 356/337, 338, 446; 250/341.1, 358.1; 600/473, 476, 407

[56] References Cited

U.S. PATENT DOCUMENTS

| | | | |
|---|---|---|---|
| 4,975,237 | 12/1990 | Brown | 356/338 |
| 5,125,404 | 6/1992 | Kittrel et al. | 128/634 |
| 5,203,339 | 4/1993 | Knüttel et al. | 128/665 |
| 5,213,105 | 5/1993 | Gratton et al. | 128/664 |
| 5,424,843 | 6/1995 | Tromberg et al. | 356/442 |
| 5,625,458 | 4/1997 | Alfano et al. | 128/665 |

*Primary Examiner*—Linda C. M. Dvorak
*Assistant Examiner*—Bryan K. Yarnell
*Attorney, Agent, or Firm*—Woodcock Washburn Kurtz MacKiewicz & Norris LLP

[57] ABSTRACT

Method and system for imaging media having spatially varying dynamic properties or spatially varying optical properties. The method and system utilizes a diffuse correlation wave which is a function of the properties of the medium. The correlation is constructed from photons which create a speckle pattern which falls on a detector at a known position with respect to the source of the photons after the photons have interacted with the media.

11 Claims, 3 Drawing Sheets

IMAGING SPATIALLY VARYING DYNAMIC MEDIA WITH DIFFUSING CORRELATION WAVES

GOVERNMENT SUPPORT

This invention was supported in part by funds from the U.S. Government (National Science Foundation Grant No. DMR93-06814) and the U.S. Government may therefore have certain rights in this invention.

FIELD OF THE INVENTION

This invention relates generally to imaging. More specifically, this invention relates to using diffusing light fluctuations to image media with spatially varying dynamic and optical intensity fluctuations.

BACKGROUND OF THE INVENTION

Imaging of the human body using visible light has long been a desirable goal. In the late 1970s, dynamic light scattering theory was applied to living tissue to measure blood flow. Multiple scattering from the blood occurred, resulting in a Doppler broadening of the laser line width as revealed by the intensity fluctuations of the remitted speckles. This type of imaging worked fairly well, since the body behaved as a static matrix, and there was only occasional scattering from moving particles within the matrix. In about 1981, Bonner and Nossal at the National Institute of Health, wrote down the theory for imaging of blood flow using light, thereby formalizing the theory of "diffusing wave spectroscopy".

By the mid-1980s, diffusing wave spectroscopy was used to image optically dense systems in which all particles are moving, but the medium is generally viewed as homogeneous; that is, there are no spatial variations in the dynamic or optical properties. The aforementioned techniques for imaging with diffuse light are therefore limited since they cannot characterize media with spatially varying, dynamic properties, but can only characterize average properties of the media with well-defined boundaries.

Therefore, the imaging art has not provided a technique for imaging heterogeneous media. The aforementioned prior imaging techniques have only been able to determine dynamic and optical characteristics of a homogeneous medium, such as a dense colloid, wherein the magnitude of fluctuation of the intensities is obtained from the temporal intensity, or the correlation from an emerging speckle.

The current theory and devices for analyzing homogeneous media do not suffice for analyzing heterogeneous fluctuating media which are analogous to tumors, burns, and other real world structures found in the human body. There thus exists a long-felt but unsatisfied need in the art for a method of imaging spatially varying dynamic media which has not heretofore been satisfied.

SUMMARY OF THE INVENTION

The aforementioned problems are solved and long-felt needs met by the present invention which in a preferred embodiment provides methods of imaging a medium having spatially varying dynamic properties or spatially varying optical properties. The methods preferably comprise the steps of irradiating the medium with a source of light which will diffuse through the medium, measuring at a detector position the temporal intensity fluctuations of photon streams that have been scattered from objects within the medium, determining the properties of the medium using measured power spectrums or temporal correlation functions, and reconstructing an image of the medium from the intensity fluctuations.

Systems for imaging a medium having spatially varying dynamic properties or spatially varying optical properties also solve the above-referenced long-felt needs. Preferably, the systems comprise a radiation source that irradiates the medium with light and for setting up a diffuse wave of photons which will scatter through the medium, a detector placed at a known position with respect to the radiation source for detecting light scattered through the medium, an analyzer interfaced to the detector for quantifying the intensity fluctuations received by the detector, thereby measuring a diffuse correlation wave, and a processor interfaced with the analyzing means for determining the properties of the medium and reconstructing an image of the medium.

The methods and systems provided in accordance with the present invention provide a significant advance in the imaging art. With the methods and systems described and claimed herein, it is possible to provide low resolution images of spatially varying, dynamic turbid media such as the human body. Such images of turbid media with spatially varying dynamic properties or spatially varying optical properties have also not been achieved in the imaging art prior to the invention of the systems and methods described herein.

The invention will be best understood by those with skill in the art by reading the foregoing detailed description of preferred embodiments of the invention in conjunction with the drawings which are first described briefly below.

DETAILED DESCRIPTION OF PREFERRED EMBODIMENTS

Figure 1:
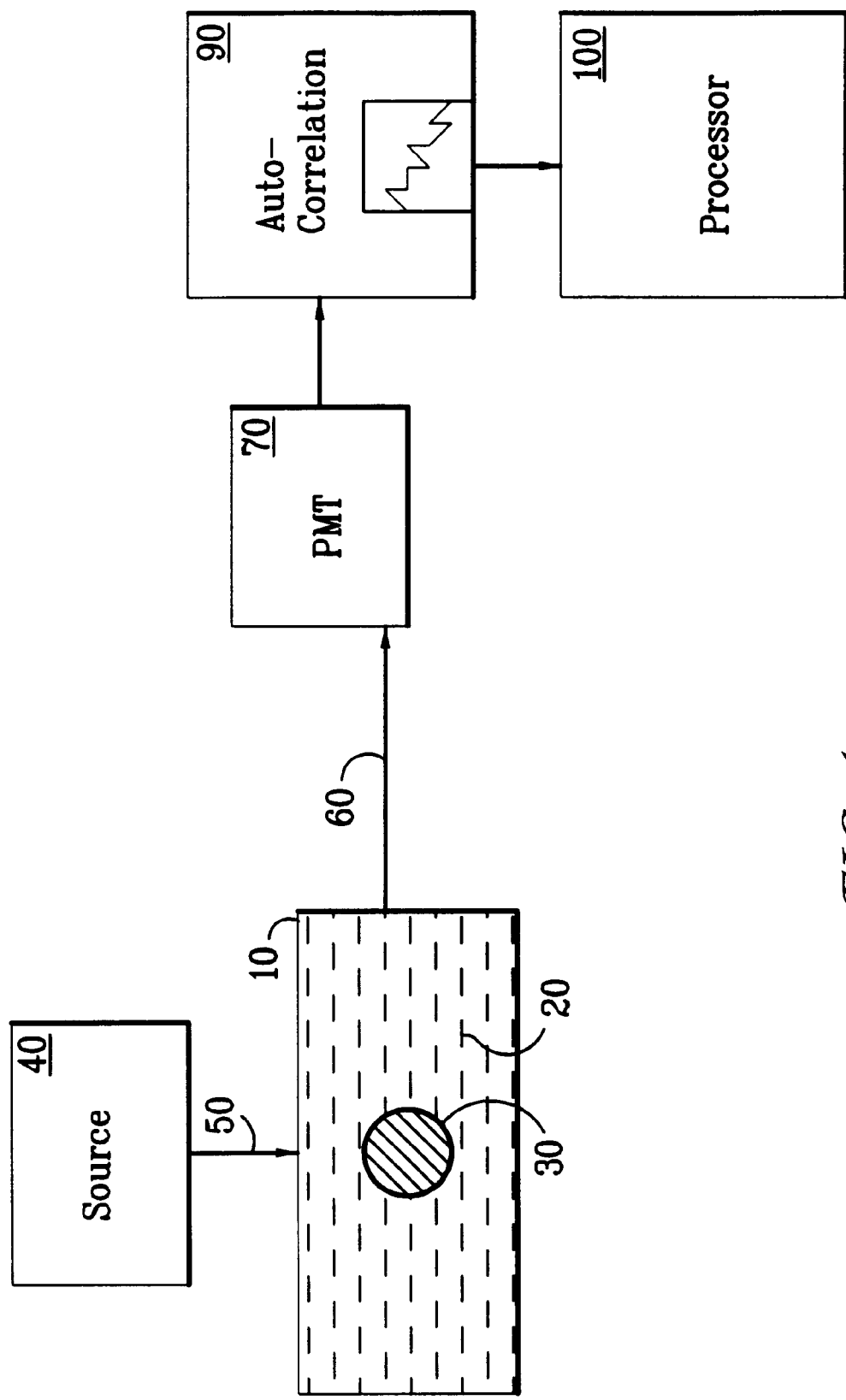
FIG. 1 is a block diagram of a system for imaging turbid media with spatially varying dynamic properties or spatially varying optical properties provided in accordance with the present invention.

Referring now to the drawings wherein like reference numerals refer to like elements, FIG. 1 is a block diagram of a system provided in accordance with the present invention for imaging media having spatially varying dynamic properties or spatially varying optical properties.

A turbid medium is shown generally at 10, and comprises a substantially heterogeneous matrix 20 wherein there is embedded an object 30. The object 30 contains small particles which are moving in a non-ordered fashion. "Non-ordered fashion" means that the particles exhibit Brownian motion, turbulent motion, shear flow, random motion or any other motion which results in a change in the relative distance between the particles. This is what is meant by the term "dynamic" throughout. In an experimental setup which has been used to verify the systems of the present invention, the matrix 20 is a solid slab of titanium dioxide suspended in resin, and the object 30 is a small cavity with a 0.2 percent suspension of 0.296 micrometer diameter polystyrene spheres. The slab has dimensions of 15×15×8 centimeters.

A source of light 40 is coupled by a multimode fiber 50 to the medium 10. Preferably, the source 40 is a coherent source of energy. Even more preferably, the source is a laser. Most preferably, the source is an argon ion laser which outputs energy in the 514 nanometer green wavelength range.

A fiber 60 is placed at a known position with respect to the matrix 20, and will pick up light which diffuses through the medium 10. A detector 70 is interfaced to the fiber, and by standard gain techniques creates a signal which is representative of the intensity fluctuations at the fiber resulting from the photons which have diffused through the medium 10 and which may have scattered from the particles in object 30. Any detector which can produce a gain, for example a photomultiplier tube, can be interfaced with the fiber 60, and it will be recognized by those with skill in the art that a fiber-detector combination will produce the results required in accordance with the invention. A preferred embodiment of fiber 60 is a single mode fiber.

In accordance with the present invention, a digital autocorrelator 90 is interfaced with the photomultiplier tube 70 in order to observe the intensity fluctuations of the signal speckle. The digital autocorrelation device 90, which is a well-known electronic system that is commercially available, measures the temporal intensity autocorrelation function of the photons received by the detector. As will be described in more detail below, this autocorrelation function can be used to obtain the scattering, absorption and dynamic characteristics of the medium in accordance with the methodology described herein.

In accordance with the invention, autocorrelation functions are measured with the source and collecting fibers individually positioned at different locations with respect to the object 30. A computer processor 100 with the appropriate software that implements the correlation diffusion theory described below determines the scattering, absorption and dynamic characteristics of the medium from the diffusion correlation wave and thereby reconstructs an image of the medium 10. The computer can be any known, standard processor which can utilize the correlation information output by the autocorrelator 90. In this manner, a reconstructed image of the medium 10 having the object 30 therein can be produced as a function of the scattering and absorption of the diffuse correlation wave as it propagates diffusing through the medium 10.

It has been demonstrated that transmissions and remission measurements of diffuse light intensity emerging from heterogeneous turbid media can provide adequate information for the construction of low resolution images of the spatially varying absorption and scattering coefficients. When the medium is dynamic, the time-dependent density fluctuations of the sample are impressed upon the temporal behavior of the diffusing light. For homogeneous fluctuating turbid media, the temporal intensity autocorrelatiLon function of an emerging speckle of diffuse light can be analyzed to provide information about the temporal fluctuations within the sample. This technique has been dubbed "diffusing wave spectroscopy". Just as diffuse photon density waves can be used to probe the spatial variations in absorption and scattering coefficients within heterogeneous media, the position-dependent measurements of the temporal autocorrelation function of diffusing light fields can be used to generate images of temporal fluctuations within heterogeneous turbid media. The techniques of the present invention provide a new contrast mechanism for imaging within turbid media. Specifically, these techniques can distinguish regions of strong and weak density fluctuations such as calcium deposits versus soft tissue or blood flow versus stasis.

CORRELATION DIFFUSION THEORY

The field and intensity temporal autocorrelation functions of coherent light emanating from a scattering medium provide information about the dynamic properties and/or the optical properties of the medium. Alternatively, it is well known that a power spectrum analysis of the light fluctuations can also be applied to characterize the dynamic properties and/or optical properties. Either embodiment may be applied in accordance with the invention.

The normalized temporal field autocorrelation function of light that has diffused through a homogeneous, turbid colloid is given by:

$$g_1(\tau) = \frac{\langle E(0)E^*(\tau) \rangle}{\langle |E|^2 \rangle} = \int_0^\infty ds P(s) \exp(-2D_s k_0^2 \tau s \mu_s'). \tag{1}$$

where E is the electric field of the emerging speckle. P(s) is the probability of a photon traveling a length s between the source and detector. $D_s$ is the diffusion coefficient of the scattering particles. $k_o$ is the wavenumber of the photon in the medium, and $\mu_s'$, is the reduced scattering factor for the diffusing photon. The brackets denote an ensemble average which, for an ergodic system is the same as a temporal average. This form for the temporal field autocorrelation function is accurate for homogeneous, fluctuating turbid media, such as a colloid. Here, homogeneous refers to the absorption, scattering, and dynamic properties of the medium.

The steady state correlation transport equation is:

$$\nabla \cdot G_1(r.\Omega.\tau)\Omega + \mu_t G_1(r.\Omega.\tau) = \mu_s \int G_1(r.\Omega'.\tau) g_1^s(\Omega,\Omega'\tau) f(\Omega.\Omega') d\Omega' + S(r.\Omega). \tag{2}$$

Here, $G_1(r,\Omega,\tau)$ is the unnormalized temporal field-autocorrelation function (i.e. $G_1(r,\Omega,\tau)=<E(0)E^*(\tau)>$) which is a function of position r, direction $\Omega$, and correlation time $\tau$. The scattering and absorption coefficients are respectively $\mu_s$ and $\mu_a$ and $\mu_t=\mu_s+\mu_a$. Furthermore, $g_1^s(\Omega,\Omega',\tau)$ is the normalized temporal field-autocorrelation function for single scattering, given by:

$$g_1^s(\Omega.\Omega'\tau) = \exp[-2D_s K_o^2 \tau (1-\Omega'.\Omega)]. \tag{3}$$

and $f(\Omega,\Omega')$ is the phase function. Finally, v is the speed of light in the medium and $S(r.\Omega)$ is the distribution of light sources. Note that when $\tau=0$ the steady state correlation transport equation is reduced to the steady state photon transport equation.

Using the $P_N$ approximation or spherical Harmonics method, a diffusion equation for correlation is derived from this more general transport equation. The correlation diffusion equation is as follows:

$$(D_p \nabla^2 - v\mu_a - 2v\mu_s' k_o^2 \tau) G_1(r.\tau) = -vS(r). \tag{4}$$

where $$D_p = \frac{v}{3\mu_s'}$$

is the photon diffusion coefficient. Notice that in the correlation diffusion equation, $G_1(r.\tau)$ is no longer a function of $\Omega$, and the reduced scattering coefficient $\mu_s'$ appears instead of the scattering coefficient $\mu_s$. For a homogeneous system, the solution of the correlation equation is identical to the solution of Eq. (1). The homogeneous solution for correlation diffusion formally has also been derived from the scalar wave equation for the electric field and the angular-averaged dynamic structure factor. The correlation diffusion equation presented here, however, is particularly useful when considering solutions for media having spatially varying dynamic properties or spatially varying optical properties.

Exact Solution Spherical Inhomogeneities

Given a piecewise homogeneous system, a solution to the diffusion equation is found by satisfying the differential equation in each homogeneous region while matching the boundary conditions at the surface between regions. An analytic solution exists for a spherical inhomogeneity embedded in an otherwise homogeneous system.

To simplify the bookkeeping, Eq. (4) can be re-written as $$(\nabla^2 + K^2(\tau))G_1(r,\tau) = -vS\delta^3(r - r_s). \quad (5)$$

where $K^2(\tau) = -3(\mu'_s + \mu_a)(\mu_a + 2\mu_s D_s k_o^2 \tau)$ and it has been assumed that a point source in space at position $r_s$. Thus, $2\mu'_s D_s k_o^2 \tau$ represents the absorption of correlation due to dynamic processes. When $\tau = 0$ there is no dynamic absorption and eq. (5) is simply reduced to the photon diffusion equation.

The solution of eq. (5) outside of a spherical inhomogeneity is $$G_1^{out}(r, \tau) = \frac{vS\exp(-K^{out}(\tau)|r - r_s|)}{4\pi|r - r_s|} + \sum_{l=o}^{\infty} A_l h_l^{(1)}(K^{out} r - r_s) Y_l^0(\theta \cdot o). \quad (6)$$

where the sphere is centered on the origin and the source is placed on the z-axis. Here, $h_1^{(1)}$ are the Hankel functions of the first kind and $Y_1^0(\theta,\phi)$ are the spherical harmonics. The coefficient $A_1$ is found by matching the appropriate boundary conditions on the surface of the sphere. These boundary conditions are the same as for photon diffusion namely $G_1^{out}(r,\tau) = G_1^{in}(r,\tau)$ and $-D_p^{out} n \cdot \nabla G_1^{out}(r,\tau) = -D_p^{in} n \cdot \nabla G_1^{in}(r,\tau)$ on the surface of the sphere, where $G_1^{in}(r,\tau)$ is the correlation function inside the spherical object and n is the normal vector to the sphere. Applying these boundary conditions:

$$A_1 = viSK^{out}(\tau)h_1^{(1)}(K^{out}(\tau)z_s) \quad (7)$$

$$Y_1^{0s}(\pi, O) \left[ \frac{D_p^{out} x j'_1(x) j_1(y) - D_p^{in} y j_1(x) j'_1(y)}{D_p^{out} x h_1^{(1)'}(x) j_1(y) - D_p^{in} y h_1^{(1)}(x) j'_1(y)} \right].$$

where $j_1$ are the spherical Bessel functions of the first kind $x = K^{out}(\tau)a$, $y = K^{in}(\tau)a$, a is the radius of the sphere $r_s = (r = Z_s \theta = \pi, \theta = 0)$, and $j_1'$ and $h_1^{(1)'}$ are the first derivatives of the functions $j_l$ and $h_1^{(1)}$ with respect to the argument.

Rytov Approximation for General Inhomogeneities

For systems with spatially varying dynamic properties, the correlation diffusion equation is approximated as:

$$(\nabla^2 + K^2(r,\tau))G_1(r,\tau) = S\delta^3(r - r_s) \quad (8)$$

where $K^2(r, \tau) = -3(\mu'_s + \mu_a)(\mu_a + 2\mu'_s D_s(r) k_o^2 \tau)$ and $D_s(r) = D_s^{avg} + \delta D_s(r)$. The average particle self-diffusion coefficient of the systems is given by $D_s^{avg}$, and $\delta D_s(r)$ are the variations with respect to this average. In this form, $K^2$ accounts for dynamics governed by Brownian motion. $K^2$ is easily modified to account for other types of dynamics as defined before.

Assuming a solution of the form $G_1(r,\tau) = U_o(r,\tau)\exp(\Phi(r,\tau))$, where $U_o(r,\tau)$ is the solution of the homogeneous correlation diffusion equation, and apply the Rytov approximation, although other approximations may also be implemented, the solution of the heterogeneous diffusion equation is:

$$U_o(r,\tau)\Phi(r,\tau) = -6(\mu'_s + \mu_a)\mu'_s k_o^2 \tau \int d^3 r' G(r',r,\tau) U_o(r',\tau) \delta D_s(r) \quad (9)$$

where $G(r',r,\tau)$ is the Green's function for the homogeneous diffusion equation. The perturbations due to any heterogeneity are thus contained in $\Phi(r,\tau)$. Measurements of the perturbed temporal field autocorrelation function using several different source-detector pairs can be used along with knowledge of the optical properties and average particle self-diffusion coefficient of the medium to determine $\delta D_s(r)$. The reconstruction is facilitated by inversion of eq. (9).

Figure 2:
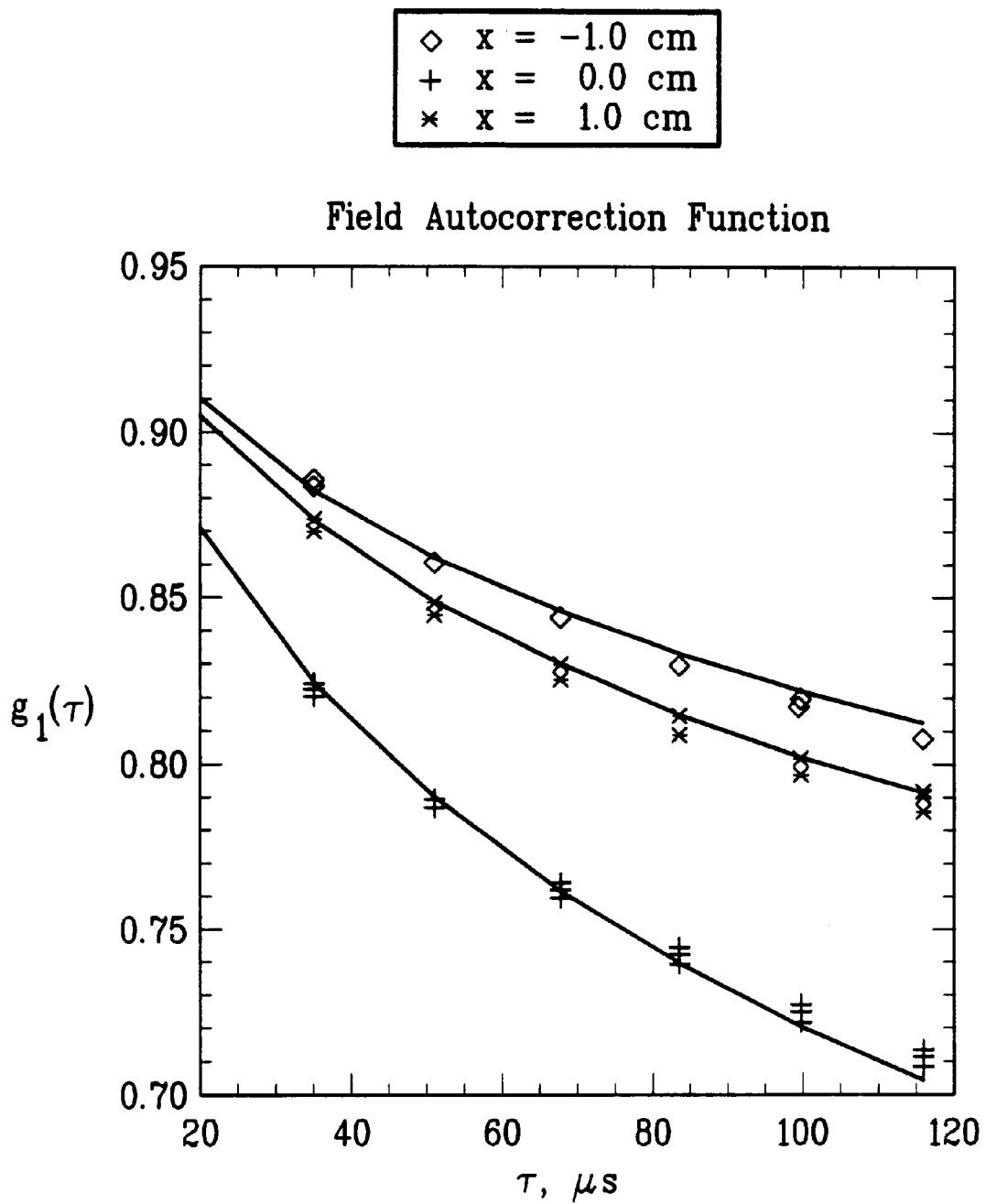
FIG. 2 is a graph of the experimental measurements of a temporal field or autocorrelation function verifying that a diffusing autocorrelation occurs.

Referring now to FIG. 2, the results of experiments show the perturbation of diffusing correlation by fluctuating spherical objects. In particular, the intensity autocorrelation function for a semi-infinite highly-scattered solid containing a spherical cavity filled with a highly-scattered colloid was measured. This simulates the human body.

The experimental apparatus is shown in FIG. 1. The light source which was the 514 nanometer line of an argon ion laser (2.5 Watts and operated with an etalon to increase the source coherence). As discussed above, the beam is coupled into a multi-mode fiber for flexibility in positioning the source on the sample. Light is collected from the sample using a single mode fiber in order to observe the intensity fluctuation of single speckles/modes. The collected light is delivered to a photon-counting photo-multiplier tube, and finally, a digital autocorrelator is used to determine the temporal intensity autocorrelation function. Autocorrelation functions are measured with the source and collecting fibers individually positioned at different locations with respect to the sphere.

The autocorrelation functions are measured at different locations with respect to the sphere by individually positioning the source and collecting fibers at different locations within the sample. Note that the temporal intensity autocorrelation function is related to the temporal field autocorrelation function by the Seigert relation:

$$g_2(\tau) = \frac{\langle I(O)I(\tau)\rangle}{\langle I^2 \rangle} = 1 + |g_1(\tau)|^2. \quad (10)$$

In FIG. 2, the measured decay of the field autocorrelation function (symbols) compared to the theoretical prediction (lines) was plotted. The correlation function for the measurement made near the fluctuating sphere decays more rapidly than when measured further from the sphere. This is expected since in the former case a large fraction of the detected photons have sampled the liquid. The difference observed between the measurements at X=+1.0 cm indicates that the sphere is not located at X=0. The theoretical best fit to the experimental data using three free parameters produced good agreement between experiment and theory and reasonable values for the free parameters. The tree parameters and the fits were: $X_o = 0.08$ cm and the optical properties of the solid $\mu_s' = 2.0$ cm$^{-1}$ and $\mu_a = 0.08$ cm$^{-1}$. The sphere was not perfectly centered at $X_o = 0.0$ cm as observed in the experimental data and the fit.

In order to reconstruct an image with a spatially varying particle diffusion coefficient, it is necessary to measure the temporal intensity autocorrelation function with several source-detector configurations so as to sample all volume elements within the sample. To generate the necessary data for the image reconstruction, the analytic solution is used for a spherical inhomogeneity embedded in an otherwise homogeneous system. The system is an infinite medium with homogeneous optical properties, $\mu_s40 =10.0$ cm$^{-1}$ $\mu_a$=0.05 cm$^{-1}$ and and D$_s$=0. A 0.5 cm diameter sphere is centered at x=0.5 cm. y=0.0 cm. and z=0.0 cm. Two different values for the object D$_s$ were used $1.0\times10^{-8}$ cm$^2$s$^{-1}$ and $5.0\times10^{-9}$ cm$^2$s$^-$.

Figure 3A:
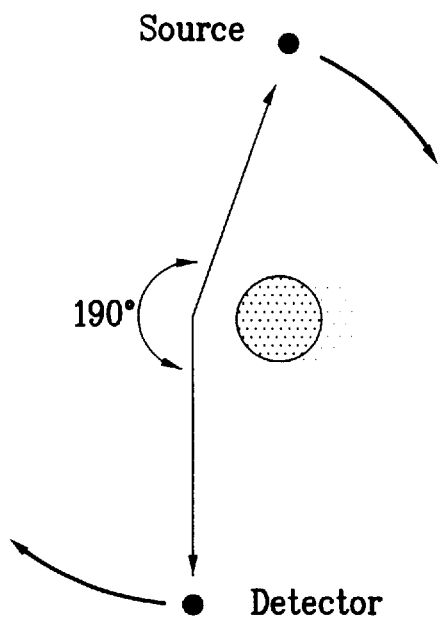
FIGS. 3A and 3B are, respectively, an example of source detector orientation for imaging a medium having spatially varying dynamic properties or spatially varying optical properties, and a model system showing the image of a spatially dynamic medium provided in accordance with the present invention.
Figure 3B:
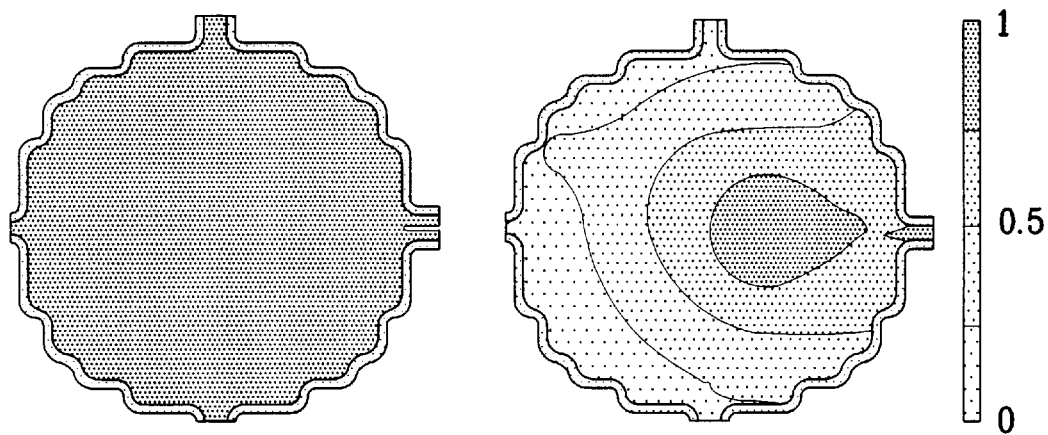

Referring to FIG. 3A, the system is illustrated to indicate the various source-detector positions relative to the spherical inhomogeneity. For each source-detector pair, the correlation function was calculated for correlation times ranging from 40 μs to 200 μs in steps of 40 μs. In FIG. 3B, The reconstructed images for the two different systems are presented. The spherical object is clearly distinguished in each case, from the grey scale we see the expected factor of two difference in the self-diffusion coefficient of the scattering particles in the sphere.

Measurements were made with a single source and detector separated by 170°. The source and detector were displaced 2.3 cm from the center of the circle and were rotated as a unit about the center of the circle, in intervals of 10°. The lightly shaded circle indicates the region reconstructed in the images presented in (b)-(c) while the dark circle indicates the actual position of the inhomogeneity. The inhomogeneity is positioned 0.5 cm laterally from the center and has a diameter of 0.5 cm. Images reconstructed with the two different values of D$_s$ for the object are presented in (b)-(c). The object D$_s$ equals $1.0\times10^{-8}$cm$^2$s$^{-1}$ and $5.0\times10^{-9}$cm$^2$s$^{-1}$ in (b) and (c) respectively. The reconstructed values for D$_s$ are $1.0\times10^{-8}$cm$^2$s$^{-1}$ and $5.0\times10^{-9}$cm$^2$s$^{-1}$ respectively normalized to indicate that the relative values were accurately reconstructed.

Diffusion photons are sensitive to the random motion of the scattering particles. This information is accessible through correlation measurements of the intensity fluctuations of a single speckle of remitted or transmitted light. Thus, the correlation diffusion equation accurately predicts the decay of the temporal intensity autocorrelation function for heterogeneous turbid media. Furthermore, it has been demonstrated that the correlation diffusion equation can be used in an imaging algorithm to reconstruct the dynamic heterogeneities of a turbid media. Sensitivity to dynamic heterogeneities can be exploited to gain contrast in identifying calcified tumors and skeletal structures, as well as distinguishing regions of the body which have varying blood flow, or which are ischemic or in stasis.

There have thus been described certain preferred embodiments of systems and methods for imaging turbid media having spatially varying dynamic properties or spatially varying optical properties provided in accordance with the present invention. While preferred embodiments have been described and disclosed, it will be recognized by those with skill in the art that modifications are within the true spirit and scope of the invention. The appended claims are intended to cover all such modifications.

What is claimed is:

1. A method for determining properties of a medium, said method comprising the steps of:

irradiating the medium with radiation that is capable of diffusing through the medium;

receiving at a detector position streams of photons scattered from objects within the medium as said radiation diffuses through the medium;

measuring at said detector position temporal intensity fluctuations of the photon streams; and determining spatially varying dynamic or optical properties of the medium based on one of (a) broadening of measured power spectrums and (b) decay of temporal correlation functions of the measured temporal intensity fluctuations.

2. The method of claim 1, comprising further the step of:

producing an image of the medium from the measured power spectrums or temporal correlation functions.

3. The method of claim 1, wherein the temporal correlation functions are temporal intensity autocorrelation functions.

4. The method of claim 1, wherein said determining step comprises using a correlation diffusion equation.

5. The method of claim 4, wherein the correlation diffusion equation is based on the equation $$\nabla \cdot G_1(r.\Omega.\tau)\Omega + \mu_t G_1(r.\Omega.\tau) = \mu_s \int G_1(r.\Omega'.\tau) g_1^s(\Omega,\Omega',\tau) f(\Omega.\Omega') d\Omega' + S(r.\Omega),$$

where $G_1(r,\Omega,\tau)$ is an unnormalized temporal field autocorrelation function, $\mu_s$ is the scattering coefficient for the scattered photon, $\mu_t$ is the absorption coefficient for the scattered photon, $g_1^s(\Omega,\Omega',\tau)$ is the normalized temporal field-autocorrelation function for single scattering, $f(\Omega,\Omega')$ is the phase function, and $S(r.\Omega)$ represents the detector position.

6. The method of claim 1, wherein the step of measuring the temporal intensity fluctuations comprises the step of counting photons received by the detector as a function of time.

7. The method of claim 1, wherein the step of measuring the temporal intensity fluctuations of the photon streams comprises the step of measuring the temporal intensity fluctuations of the photon streams at a plurality of detector positions.

8. The method of claim 1, wherein the radiation is light.

9. The method of claim 1, wherein the radiation is a continuous waveform.

10. The method of claim 1, wherein the radiation is unmodulated.

11. A system for producing an image of a medium, said system comprising:

a radiation source that irradiates a medium with radiation that is capable of diffusing through the medium, wherein the radiation source sets up a diffuse wave of photons which scatter through the medium;

a detector placed at a known position with respect to the radiation source, said detector detecting streams of photons scattered from objects within the medium as said radiation diffuses through the medium;

an analyzer, coupled to the detector, that measures temporal intensity fluctuations of the photon streams received by the detector;

a processor, coupled to the analyzer, that determines spatially varying dynamic or optical properties of the medium based on one of (a) broadening of measured power spectrums and (b) decay of temporal correlation functions of the measured temporal intensity fluctuations, and produces an image of the medium from the measured power spectrums or temporal correlation functions; and a display, coupled to said processor, for displaying said image.

* * * * *

UNITED STATES PATENT AND TRADEMARK OFFICE
CERTIFICATE OF CORRECTION

PATENT NO. : 6,076,010
DATED : June 13, 2000
INVENTOR(S) : Boas, et. al.

It is certified that error appears in the above-identified patent and that said Letters Patent is hereby corrected as shown below:

On the title page, under ABSTRACT, first line thereof, please delete "Method and system" and insert –Methods and systems– therefor.

On the title page, under ABSTRACT, third line thereof, please delete "method and system utilizes" and insert –methods and systems utilize– therefor.

In column 3, line 53, please delete "autocorrelatiLon" and insert --autocorrelation-- therefor.

In column 4, line 49, please delete "Harmonics" and insert --harmonics-- therefor.

In column 4, line 54, please delete "$(D_p\nabla^2-v\mu_a-2v\mu' k_o^2\tau)G_1(r.\tau)=-vs(r)$" and insert -- $(D_p\nabla^2-v\mu_a-2v\mu'_a D_s k_o^2\tau)G_1(r.\tau)=-vs(r)$ –therefor.

In column 5, line 17, please delete "$(\mu_a + 2\mu_a D_s k_o^2\tau)$ and insert $\mu_a + 2\mu'_a D_s k_o^2\tau$ -- therefor.

In column 6, line 7, please delete "$U_o(r,t)\varphi(r,t) = -6(\mu'_a+\mu_a)\mu'_s k_o^2\tau \int d^3r'G(r',r,\tau)U_o(r',\tau\delta D_s(r)$" and insert --$U_o(r,t)\varphi(r,t) = -6(\mu'_a+\mu_a)\mu'_s k_o^2\tau \int d^3r'G(r',r,\tau)U_o(r',\tau)\delta D_s(r)$– therefore.

In column 6, line 54, please delete "x = + 1.0 cm" and insert --x = $\pm$ 1.0 cm– therefor.

In column 6, line 58, please delete "tree" and insert –free–.

Signed and Sealed this

Twenty-second Day of May, 2001

Attest:

NICHOLAS P. GODICI

*Attesting Officer*     *Acting Director of the United States Patent and Trademark Office*